US00PP16712P3

(12) United States Plant Patent
Lal et al.

(10) Patent No.: US PP16,712 P3
(45) Date of Patent: Jun. 27, 2006

(54) **CITRAL RICH HIGH YIELDING LEMONGRASS PLANT 'NIMA' OF *CYMBOPOGON FLEXUOSUS***

(50) Latin Name: *Cymbopogon flexuosus*
Varietal Denomination: Poaceae

(75) Inventors: Raj Kishori Lal, Lucknow (IN); Hari Om Misra, Lucknow (IN); Jawahar Ram Sharma, Lucknow (IN); Nilakshi Singh, Lucknow (IN); Ajit Kumar Shasany, Lucknow (IN); Ali Arif Naqvi, Lucknow (IN); Janak Raj Bahl, Lucknow (IN); Arun Prasad, Lucknow (IN); Suman Preet Singh Khanuja, Lucknow (IN)

(73) Assignee: Council of Scientific & Industrial Research, New Dehli (IN)

( * ) Notice: Subject to any disclaimer, the term of this patent is extended or adjusted under 35 U.S.C. 154(b) by 27 days.

(21) Appl. No.: 10/401,753

(22) Filed: Mar. 31, 2003

(65) Prior Publication Data

US 2004/0194175 P1 Sep. 30, 2004

(51) Int. Cl.
*A01H 5/00* (2006.01)

(52) U.S. Cl. ..... Plt./258
(58) Field of Classification Search ..... Plt./258
See application file for complete search history.

*Primary Examiner*—Anne Marie Grunberg
(74) *Attorney, Agent, or Firm*—Birch, Stewart, Kolasch & Birch, LLP

(57) ABSTRACT

A new and distinct high essential oil variety of lemongrass (*Cymbopogon flexuosus*) is named 'Nima'. Further, the invention relates to the high content of the monoterpene citral in the essential oil. This novel variety 'Nima' of lemongrass is a selection from the open pollinated seedlings of the seeds obtained from another *Cymbopogon flexuosus* variety OD 19 from the germ plasm collection of CIMAP. This variety is propagated through vegetative means using the slips and is stable for commercial cultivation.

2 Drawing Sheets

Latin name of the genus and species of the plant claimed: *Cymbopogon flexuosus.*

Variety denomination: The claimed plant is a species of East Indian lemongrass Poaceae.

BACKGROUND OF THE INVENTION

Lemongrass (*Cymbopogon flexuosus*), family—Poaceae is an aromatic grass species and is commonly known as 'East Indian Lemongrass'. It is a vegetatively (also seed) propagated perennial, multicut crop in the tropics. The prefix 'Lemon' owes to its typical lemon-like odor, released from leaves on maceration, which is mainly due to the presence of citral as a cyclic monoterpene. The lemongrass oil as such is widely used in perfumes, soaps and cosmetics to obtain typical lemon notes. Beside, it's an important source of citral, which is used in perfumes and medicine. While citral forms a significant raw material for confectionery and beverages, it is the principal source of β-ionone which is extensively used for the synthesis of vitamin A and a number of a chemicals including synthetic violet perfumes. Due to the limited improved varieties for high oil yield and citral content, its cultivation is not popular among farmers. Therefore, there is a need to develop superior varieties of lemongrass for high oil yield and citral content.

SUMMARY OF THE INVENTION

An object of the invention is, therefore, to develop a new and distinct high oil rich in citral contents variety of lemongrass (*Cymbopogon flexuosus*) which can produce high amount of lemongrass oil with high citral content.

The present invention relates to a new and distinct high essential oil variety of lemongrass (*Cymbopogon flexuosus*) named as 'Nima'. Further the invention relates to the high content of the monoterpene citral in the essential oil. This novel variety 'Nima' of the lemongrass is a selection from the open pollinated seedlings of the seeds obtained from another *Cymbopogon flexuosus* variety OD 19 from the germplasm collection of CIMAP.

Asexual reproduction first occurred in Korala, India, when slips were vegetatively reproduced and found stable for commercial cultivation.

BRIEF DESCRIPTION OF THE DRAWINGS

FIG. 1 shows the plant 'Nima' in the field.

FIG. 2 shows unique RAPD profile of 'Nima' Lane 1: 1 Hind III+EcoRI marker. Lane 2–15: Profiles with primers MAP 01, MAP 02, MAP 04, MAP 05, MAP 06, MAP 09, MAP 10, MAP 11, MAP 12, MAP 15, MAP 16, MAP 17, MAP 18, MAP 19.

DETAILED BOTANICAL DESCRIPTION

The present invention provides a new and distinct variety of *Cymbopogon flexuosus* 'Nima' producing high essential oil, rich in citral and the variety is characterized by the morphological/agronomic features as described in Table 1.

TABLE 1

Morphological/agronomic feature of var. Nima.

| Attributes | Elite clone/strain CIMAP/S 49 (NIMA) | Checks PRAGATI | PRAMAN | CKP 25 |
|---|---|---|---|---|
| Plant height (cm) | 100.00 | 145.00 | 125.00 | 160.00 |
| Growth habit | Closed/erect | open | semi closed | semi open |
| No. of tillers/plant | 65 | 45 | 50 | 55 |
| *Herb yield/year (q/ha) | 289 | 215 | 240 | 185 |
| *Oil content (%) | 0.86 | 0.57 | 0.56 | 0.93 |
| *Oil yield (kg/ha) | 248 | 122 | 124 | 172 |
| *Citral (%) | 89.06 | 82.04 | 82.23 | 79.07 |

*Average of the mean of the two years in Pilot Trial

The strain CIMAP/S-49 (henceforward referred to as 'Nima') has medium tall height, with small, dark purple tinged stem, high number of tillers/plant and dark green broad leaves as the distinct morphological features (color categories are described later). The relative performance of 'Nima' in different yield evaluation trails is presented in the following Table 2.

TABLE 2

Mean performance ($\bar{X}$) of elite clones over years in different yield trials of lemongrass*

| S.No. | Entries | Herb yield IET (g/plot) | BST (kg/plot) | PST (ql/ha/year) | Oil content (%) IET | BST | PST |
|---|---|---|---|---|---|---|---|
| 1. | CIMAP/S 49 | 0.56 | 9.32 | 289 | 0.79 | 0.89 | 0.86 |
| 2. | CIMAP/K 1 | 0.47 | 6.92 | — | 0.32 | 0.53 | — |
| 3. | CIMAP/A 4 | 0.81 | — | — | 0.46 | — | — |
| 4. | CIMAP/S 21 | 0.26 | 6.67 | — | 0.44 | 0.39 | — |
| 5. | CIMAP/S 1 | 0.31 | 7.22 | — | 0.62 | 0.55 | — |
| 6. | CIMAP/S 40 | 0.29 | 8.01 | — | 0.70 | 0.68 | — |
| 7. | Pragati (C) | 0.30 | 6.11 | 215 | 0.47 | 0.62 | 0.57 |
| 8. | Praman(C) | 0.43 | 6.58 | 240 | 0.50 | 0.63 | 0.56 |
| 9. | OD19(Parent) | 0.29 | 5.40 | — | 0.52 | 0.56 | — |
| 10. | Krishana(C) | 0.24 | 6.48 | — | 0.93 | 0.94 | — |
| 11. | Cauvery(C) | 0.24 | 4.67 | — | 0.65 | 0.70 | — |
| 12. | CKP 25(C) | 0.34 | 6.87 | 185 | 0.87 | 0.98 | 0.93 |
| CD | (5%) | 0.17 | 1.54 | — | 0.07 | 0.25 | — |
| | (1%) | 0.23 | 2.06 | — | 0.18 | 0.18 | — |

| S.No. | Entries | Oil yield IET (g/plot) | BST (g/plot) | PST (kg/ha/year) | Citral content (%) IET | BST | PST |
|---|---|---|---|---|---|---|---|
| 1. | CIMAP/S 49 | 4.13 | 82.32 | 248 | 89.58 | 90.32 | 89.06 |
| 2. | CIMAP/K 1 | 1.51 | 37.46 | — | 60.17 | 81.31 | — |
| 3. | CIMAP/A 4 | 3.73 | — | — | 2.64 | — | — |
| 4. | CIMAP/S 21 | 1.22 | 25.89 | — | 82.53 | 71.68 | — |
| 5. | CIMAP/S 1 | 1.94 | 56.71 | — | 83.23 | 89.24 | — |
| 6. | CIMAP/S 40 | 2.07 | 53.56 | — | 85.23 | 85.29 | — |
| 7. | Pragati (C) | 1.39 | 34.32 | 122 | 84.03 | 82.70 | 82.04 |
| 8. | Praman(C) | 2.10 | 39.59 | 124 | 79.97 | 77.75 | 82.23 |
| 9. | OD19(Parent) | 1.45 | 29.15 | — | 83.50 | 84.72 | — |
| 10. | Krishana(C) | 2.18 | 56.66 | — | 80.53 | 79.53 | — |
| 11. | Cauvery(C) | 1.55 | 27.00 | — | 81.17 | 79.36 | — |
| 12. | CKP 25(C) | 3.25 | 70.29 | 172 | 77.27 | 77.65 | 79.07 |
| CD | (5%) | 10.56 | 10.30 | — | 1.27 | 7.42 | — |
| | (1%) | 14.35 | 13.09 | — | 1.73 | 9.99 | — |

TABLE 2-continued

Mean performance ($\bar{X}$) of elite clones over years in different yield trials of lemongrass*

*IET (Initial Evaluation Trial)-RBD design with three replications; Plot size −0.50 $m^2$ for the one year (1996–97) with three harvestings; BST (Bench Scale Trial)-RBD design with three replications; Plot size −3.75 $m^2$ for the two years (1997–98 & 1998–99) with six harvestings in two years; PST (Pilot Scale Trial or Large scale Trial); Plot size −100 $m^2$ for the two years (1998–99 to 1999–2004) with six harvestings in two years; C- Checks.

The herb yield of 'Nima' is shown in Table 3.

TABLE 3

Herb Yield

| S.No. | Entries | IET (g/plot) | BST (kg/plot) | PST (ql/ha/year |
|---|---|---|---|---|
| 1. | CIMAP/S49 (NIMA) | 0.56 | 9.32 | 289 |
| 9. | OD19 (Parental variety) | 0.29 | 5.40 | **inferior |

| S.No. | Entries | IET | BST | PST |
|---|---|---|---|---|
| Oil content (%): | | | | |
| 1. | CIMAP/S49 (NIMA) | 0.79 | 0.89 | 0.86 |
| 9. | OD19 (Parental variety) | 0.52 | 0.56 | **inferior |

| S.No. | Entries | IET (g/plot) | BST (g/plot) | PST (kg/ha/year) |
|---|---|---|---|---|
| Oil yield: | | | | |
| 1. | CIMAP/S49 (NIMA) | 4.13 | 82.32 | 248 |
| 9. | OD19 (Parental variety) | 1.45 | 29.15 | **inferior |

| S.No. | Entries | IET | BST | PST |
|---|---|---|---|---|
| Citral content (%): | | | | |
| 1. | CIMAP/S49 (NIMA) | 89.58 | 90.32 | 89.06 |
| 9. | OD19 (Parental variety) | 83.50 | 84.72 | **inferior |

*IET (Initial Evaluation Trial)-RBD design with three replications; Plot size −0.50 $m^2$ for the one year (1996–97) with three harvestings; BST (Bench Scale Trial)-RBD design with three replications; Plot size −3.75 $m^2$ for the two years (1997–98 & 1998–99) with six harvestings in two years; PST (Pilot Scale Trial); Plot size −100 $m^2$ for the two years (1998–99 to 1999–2004) with six harvestings in two years;
**Inferior and Dropped due to low yield

Taxonomic Description of the Plant 'Nima'

The aromatic perennial grass 'Nima' (family-Poaceae) attains a height up to 100 cm. The morphological description has been provided below:

1. Genus: *Cymbopogon.*
2. Species: *flexeosus L.*
3. Family: Poaceae.
4. Common name: Lemongrass.
5. Plant height: 100.00 cm.
6. Growth habit: Erect and bushy.
7. Stem: Culm, Moderately bold Rudimentary, leaves coming out in whorls.
   *Thickness.*—1.0 to 2.0 cm.
   *Number of tillers per plant.*—55 to 70.
   *Number of leaves per tiller.*—6 to 15.
   *Colour.*—Yellow Green Group (145D).
8. Leaf: Sheathed, sessile.
   *Colour of upper surface.*—Green Group (137B).
   *Colour of lower surface.*—Green Group (137A).

*Texture.*—Rough.
*Surface.*—Glabrous.
*Shape.*—Linear.
*Margin.*—Undulating.
*Tip.*—Acuminate.
*Base.*—Attenuate.
*Leaf sheath.*—Purple group (79A) upper surface, Grayed green (139A) lower surface with purple streaks (79A).
*Area.*—82.55 sq cm.
*Length.*—40 to 80 cm leaf lamina, 15 to 25 cm leaf sheath.
*Width.*—1.5 to 2.5 cm leaf lamina, 1.0 to 1.5 cm leaf sheath.

9. Inflorescence: Panicle.
*Florets.*—Purple violet (80C), Glumes 3.0 to 3.5 mm, Awns 11.0 to 14.0 mm long, lowest pedicle of sessile spikelet is slightly swollen and connate to the base of rachis.
*Arrangement.*—Racemose.
*Time to flowering.*—February.
*Lastingness of bloom.*—February to April.
*Seeds.*—Purple violet (80C).
10. Oil content in the fresh herb (%): 0.8 to 0.9.
11. Oil quality:
*Citral.*—85.0 to 90.0%.
*Limonene.*—0.1 to 0.5%.
*Linalool.*—0.1 to 0.5%.
*Geraniol.*—1.0 to 2.0%.
*Geranyl acetate.*—0.5 to 1.5%.

Herbage (shoot biomass): 150 to 300 quintal/ha/year.

In summary, the glume color is purple violet (80C), the awn color is purple (79A), the seed color is purple violet (80C) and the seeds are sterile.

The color codes are according to The R.H.S. Color Chart published by The Royal Horticultural Society, 80 Vincent Square, London SW1P 2PE, 1995.

Breeding History Of 'Nima'

The vegetative slips of *Cymbopogon flexuosus* 'OD-19' (a released variety of lemongrass from Lemongrass Research Center, Odakalli, Kerala, India) were obtained from the National Gene Bank of Medicinal and Aromatic plants housed at Central Institute of Medicinal and Aromatic Plants, Lucknow. These were grown in the field of CIMAP in the year 1994–1995 and the seedlings obtained from the seeds of 'O.D. 19' were primarily screened for high herb and oil yield with high citral content in the year 1995–1996. The slips were planted in the month of July and harvested 3 times in the year in 4 months interval. Fresh leaves were collected during the harvesting from the field grown plants, and oil was extracted from 100 g plant samples in 3 replicates by hydro-distillation using Clevenger's apparatus. Oil content in terms of oil percentage was calculated as the mean of 3 samples.

GLC analysis for major oil constituents was performed on a Varian CX-3400 using a 30m × 0.25 mm (0.25m) Supelcowax-10 column. The injector and detector temperature were maintained at 200 and 225° C. respectively, with oven temperature programmed from 60 to 200° C. at the rate of 7° C. $min^{-1}$ increase, with initial and final holds of 2 and 5 minutes respectively. Hydrogen gas was used as carrier at the rate of 1 ml $min^{-1}$ and 0.1 ml of sample was injected with a split ratio of 1:50. Data were processed in the electronic integrator Varian 4400 and the identification was based on retention time of spiked authentic samples of different compounds and retention indices calculations. As a result, six superior plants (CIMAP/S 49, CIMAP/ K1, CIMAP/A4, CIMAP/S1, CIMAP/S21 and CIMAP/S40) were identified for above parameters.

The plants were then evaluated in Initial Evaluation Trial (IET) during 1996–1997 along with six checks (released varieties) 'OD 19', 'Pragati', 'Praman', 'Krishna', 'Cauvery' and 'CKP 25', where the five clones, namely CIMAP/S 49, CIMAP/ K1, CIMAP/S1, CIMAP/S21 and CIMAP/S40 were found to be highly promising for high herb, oil yield and better quality of essential oil. Then, these superior selected clones were evaluated in bench scale trials (BST) for two years where these were compared to all the checks during 1997–1998 and 1998–1999. The high herb and oil yielding clone CIMAP/S 49 with high citral content was then placed in pilot scale trials (PST) for two years along with three best check varieties ('Pragati', 'Praman', and 'CKP 25') during 1998–1999 and 1999–2000. This elite clone/strain CIMAP/S 49 maintained its superiority over all the checks for herb, oil yield and citral content. The elite strain was named as variety 'Nima'.

Yield trials were conducted at CIMAP's farm, Lucknow (UP, India) and herbage, oil yield and citral content were observed to be higher (as in Table 2) in the new genotype 'Nima', in comparison to other existing varieties. Similarly, no variants of any kind have been observed since 1997–2000 until the date of filing the patent, indicating the stability and uniformity of the genotype. Further, the comparative herbage and oil yields of 'Nima' were significantly higher in comparison to other varieties/genotypes in different years and seasons. The plant can be multiplied vegetatively for propagation through slips for commercial cultivation, can be grown in monoculture, and another crop may follow after harrowing the field with the disk harrow.

Plants of this variety are propagated through only vegetative means using the slips, and the plants are stable for commercial cultivation.

In summary, The OD 19 variety is propagated by clones (vegetative slips/tillers) where the heterozygosity and genetic variability have fixed means, and there is no segregation if grown by vegetative means (normal practice). For the purpose of breeding, growing this variety by seeds produces a tremendous segregation in the seedlings. The inventors elucidated this type of variability in their experiments.

1. By the evaluation of seedlings for high herb with better quality oil, six superior plants (CIMAP/S 49, CIMAP/ K1, CIMAP/A4, CIMAP/S1, CIMAP/S21 and CIMAP/S40) were identified for the parameters described above. They were then evaluated in an initial evaluation trial (IET) during 1996–1997 along with six checks (released varieties) 'OD 19', 'Pragati', 'Praman', 'Krishna', 'Cauvery' and 'CKP 25'.
2. The five clones, namely CIMAP/S 49, CIMAP/K 1, CIMAP/S1, CIMAP/S21 and CIMAP/S40, were found to be highly promising for high herb, oil yield and better quality of essential oil.
3. These superior selected clones were then evaluated in Bench Scale Trial (BST) for two years where these were compared to all the checks during 1997–1998 and 1998–1999.
4. The high herb and oil yielding clone CIMAP/S 49 with high citral content was then placed in Pilot Scale Trials (PST) for two years along with the three best check varieties ('Pragati', 'Praman', and 'CKP 25') during 1998–1999 and 1999–2000.

5. This elite clone/strain CIMAP/S 49 maintained its superiority over all the checks for herb, oil yield and citral content.

6. The elite strain was named as variety 'Nima.'

Yield trials were conducted at CIMAP's farm, Lucknow (UP, India).

Accordingly, the invention provides a new and distinct citral-rich variety of lemongrass that can be stably propagated through vegetative means and has the following combinations of characteristics establishing as distinctiveness from the known varieties of *Cymbopogon flexuosus:* a. Greenish upper surface (137B), greenish lower surface (137A) Purple violet (80C) florets, and rudimentary culms supporting the leaves in whorls.

b. Randomly amplified polymorphic DNA (RAPD) profile for polymerized chain reaction(PCR)amplified DNA segment using 14 primers distinct from the other existing varieties.

c. Highest biomass (250 to 300 q/ha/year) and highest oil yield (220 to 260 kg/ha/year) in comparison to other available checks.

d. Highest citral content (85 to 90%) in comparison to other genotypes.

e. Essential oil with the combination of moterpenes like Citral: 85.0 to 90.0%, Limonene: 0.1 to 0.5%, Linalool: 0.1 to 0.5%, Geraniol: 1:0 to 2.0%, Geranyl acetate: 0.5 to 1.5% in addition to other unidentified monoterpene fractions totaling to 100%.

The genotype 'Nima' possesses a green (137B) colored upper surface, a green (137A) lower surface (FIG. 1) and purple (80C) colored florets. The genotype 'Nima' produces the highest biomass (250 to 300 q/ha/year) and the highest oil yield (220 to 260 kg/ha/year) in comparison to other available checks. The citral content of the new genotype is higher (85 to 90%) in comparison to other genotypes.

RAPD Analysis

The protocol of Khanuja et al. (1999) (Khanuja, SPS, Shasany, AK, Darokar, MP, Kumar S., 1999. Rapid isolation of PCR amplifiable DNA from the dry and fresh samples of plants producing large amounts of secondary metabolites and essential oils by modified CTAB procedure. Plant Molecular Biology Reporter. 17, 74) was employed to isolate DNA from fresh leaf tissue. A small amount of isolated DNA was used to set up polymerase chain reaction (PCRs) in 25 μl volume. A reaction tube contained 25 ng of DNA, 0.2 unit of Taq DNA polymerase, 100 μM each of dNTPs, 1.5 mM $MgCl_2$ and 5 pmol of decanucleotide primers. 3 sets of 20 primers each were used to assess the genetic variability among the 18 accessions. The decanucleotide primers were custom synthesized in the laboratory at CIMAP using ABI 392 model synthesizer (Applied Biosystems). The amplified products were separated on 1.2% agarose gel containing 0.5 μg $ml^{-1}$ of ethidium bromide and photographed with Image Master® VDS (Pharmacia). The bands were analyzed using Image master ID elite software v 3.00. This above-described methodology was typically used in C of the MAP 02 in the RAPD pattern below.

The genotype Nima is distinct in its RAPD profile in comparison to 'Pragati', 'Praman', 'CKP25' and 'Krishana'. Though the genotype 'Nima' was a seed progeny of the released variety 'OD 19', the RAPD pattern still was different from the parent, which indicates gross genome rearrangements in the new genotype.

The random primers used for developing the RAPD pattern are as follows:

| Primers | Base sequence | |
|---|---|---|
| MAP 01 | 5' AAA TCG GAG C 3' | (SEQ ID NO: 1) |
| MAP 02 | 5' GTC NTA CTC G 3' | (SEQ ID NO: 2) |
| MAP 04 | 5' TGC GCG ATC G 3' | (SEQ ID NO: 3) |
| MAP 05 | 5' AAC GTA CGC G 3' | (SEQ ID NO: 4) |
| MAP 06 | 5' GCA CGC CGG A 3' | (SEQ ID NO: 5) |
| MAP 09 | 5' CGG GAT CCG C 3' | (SEQ ID NO: 6) |
| MAP 10 | 5' GCG AAT TCC G 3' | (SEQ ID NO: 7) |
| MAP 11 | 5' CCC TGC AGG C 3' | (SEQ ID NO: 8) |
| MAP 12 | 5' CCA AGC TTG C 3' | (SEQ ID NO: 9) |
| MAP 15 | 5' AAG ATA GCG G 3' | (SEQ ID NO: 10) |
| MAP 16 | 5' GGA TCT GAA C 3' | (SEQ ID NO: 11) |
| MAP 17 | 5' TTG TCT CAG G 3' | (SEQ ID NO: 12) |
| MAP 18 | 5' CAT CCC GAA C 3' | (SEQ ID NO: 13) |
| MAP 19 | 5' GGA CTC CAC G 3' | (SEQ ID NO: 14) |

(MAP—Medicinal and Aromatic Plants)

Using the above primers, the distinct RAPD profile of the new genotype 'Nima' was deduced (FIG. 2).

The genotype 'Nima' or the variety 'Nima' was developed at the Central Institute of Medicinal and Aromatic Plants (CIMAP), Lucknow, which is a constituent of the Council of Scientific and Industrial Research (CSIR), India under the genetic improvement programme of lemongrass. The complete RAPD profile for PCR amplified DNA using 14 primers (as mentioned earlier) is available providing evidence of distinctiveness of the genotype 'Nima'.

After ascertaining the distinctiveness of the genotype 'Nima' from the progenitor 'OD 19' through RAPD, profiling the analysis was narrowed down to 'Pragati', 'Praman', 'CKP25' and 'Krishana' for comparison. Genotypic pair analysis was used for assessing the genetic/molecular distances. The following Table 4 gives the extent of similarity among these five genotypes in paired testing.

TABLE 4

Similarity indices (Percentage/100) for commonality of amplified bands (paired analysis)

| | Pragati | Praman | CKP 25 | Nima | Krishna |
|---|---|---|---|---|---|
| Pragati | 1.000 | | | | |
| Praman | 0.481 | 1.000 | | | |
| CKP 25 | 0.423 | 0.602 | 1.000 | | |
| Nima | 0.674 | 0.462 | 0.524 | 1.000 | |
| Krishna | 0.724 | 0.484 | 0.518 | 0.785 | 1.000 |

From this analysis, the genotype 'Nima' was found to be 21.5% to 53.8% diverse compared to the check varieties and hence completely new and distinct.

SEQUENCE LISTING

<160> NUMBER OF SEQ ID NOS: 14

<210> SEQ ID NO 1
<211> LENGTH: 10
<212> TYPE: DNA
<213> ORGANISM: Artificial Sequence
<220> FEATURE:
<223> OTHER INFORMATION: Random MAP primer

<400> SEQUENCE: 1 aaatcggagc 10

<210> SEQ ID NO 2
<211> LENGTH: 10
<212> TYPE: DNA
<213> ORGANISM: Artificial Sequence
<220> FEATURE:
<223> OTHER INFORMATION: Random MAP primer
<220> FEATURE:
<221> NAME/KEY: misc_feature
<222> LOCATION: (4)..(4)
<223> OTHER INFORMATION: n is a, c, g, or t

<400> SEQUENCE: 2 gtcntactcg 10

<210> SEQ ID NO 3
<211> LENGTH: 10
<212> TYPE: DNA
<213> ORGANISM: Artificial Sequence
<220> FEATURE:
<223> OTHER INFORMATION: Random MAP primer

<400> SEQUENCE: 3 tgcgcgatcg 10

<210> SEQ ID NO 4
<211> LENGTH: 10
<212> TYPE: DNA
<213> ORGANISM: Artificial Sequence
<220> FEATURE:
<223> OTHER INFORMATION: Random MAP primer

<400> SEQUENCE: 4 aacgtacgcg 10

<210> SEQ ID NO 5
<211> LENGTH: 10
<212> TYPE: DNA
<213> ORGANISM: Artificial Sequence
<220> FEATURE:
<223> OTHER INFORMATION: Random MAP primer

<400> SEQUENCE: 5 gcacgccgga 10

<210> SEQ ID NO 6
<211> LENGTH: 10
<212> TYPE: DNA
<213> ORGANISM: Artificial Sequence
<220> FEATURE:
<223> OTHER INFORMATION: Random MAP primer

<400> SEQUENCE: 6

-continued cgggatccgc 10

<210> SEQ ID NO 7
<211> LENGTH: 10
<212> TYPE: DNA
<213> ORGANISM: Artificial Sequence
<220> FEATURE:
<223> OTHER INFORMATION: Random MAP primer

<400> SEQUENCE: 7 gcgaattccg 10

<210> SEQ ID NO 8
<211> LENGTH: 10
<212> TYPE: DNA
<213> ORGANISM: Artificial Sequence
<220> FEATURE:
<223> OTHER INFORMATION: Random MAP primer

<400> SEQUENCE: 8 ccctgcaggc 10

<210> SEQ ID NO 9
<211> LENGTH: 10
<212> TYPE: DNA
<213> ORGANISM: Artificial Sequence
<220> FEATURE:
<223> OTHER INFORMATION: Random MAP primer

<400> SEQUENCE: 9 ccaagcttgc 10

<210> SEQ ID NO 10
<211> LENGTH: 10
<212> TYPE: DNA
<213> ORGANISM: Artificial Sequence
<220> FEATURE:
<223> OTHER INFORMATION: Random MAP primer

<400> SEQUENCE: 10 aagatagcgg 10

<210> SEQ ID NO 11
<211> LENGTH: 10
<212> TYPE: DNA
<213> ORGANISM: Artificial Sequence
<220> FEATURE:
<223> OTHER INFORMATION: Random MAP primer

<400> SEQUENCE: 11 ggatctgaac 10

<210> SEQ ID NO 12
<211> LENGTH: 10
<212> TYPE: DNA
<213> ORGANISM: Artificial Sequence
<220> FEATURE:
<223> OTHER INFORMATION: Random MAP primer

<400> SEQUENCE: 12 ttgtctcagg 10

<210> SEQ ID NO 13
<211> LENGTH: 10
<212> TYPE: DNA

-continued

```
<213> ORGANISM: Artificial Sequence
<220> FEATURE:
<223> OTHER INFORMATION: Random MAP primer

<400> SEQUENCE: 13

catcccgaac                                                          10


<210> SEQ ID NO 14
<211> LENGTH: 10
<212> TYPE: DNA
<213> ORGANISM: Artificial Sequence
<220> FEATURE:
<223> OTHER INFORMATION: Random MAP primer

<400> SEQUENCE: 14

ggactccacg                                                          10
```

What is claimed:

1. A plant as described and illustrated herein, said plant being a lemongrass (*Cymbopogon flexuosus*) having the following characteristics:

a) greenish upper surface (137B), greenish lower surface (137A) purple violet (80C) florets, and rudimentary culms supporting the leaves in whorls, b) yield of biomass of 250 to 300 q/ha/year and yield of oil of 220 to 260 kg/ha/year, c) citral content of the oil of 85 to 90%, d) produces an essential oil having a monoterpene content of: 85.0 to 90.0% citral, 0.1 to 0.5% limonene, 0.1 to 0.5% linalool, 1.0 to 2.0% geraniol, 0.5 to 1.5% geranyl acetate in addition to other unidentified monoterpene fractions totaling to 100%.

* * * * *

Figure 1 shows the plant 'Nima' in the field
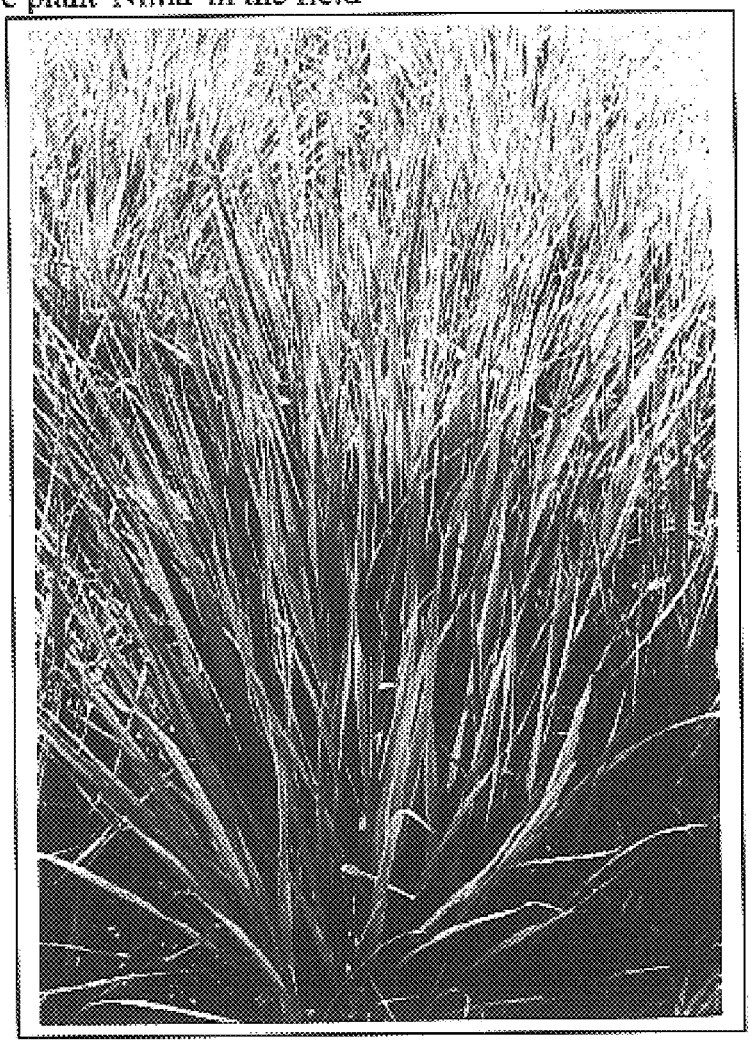

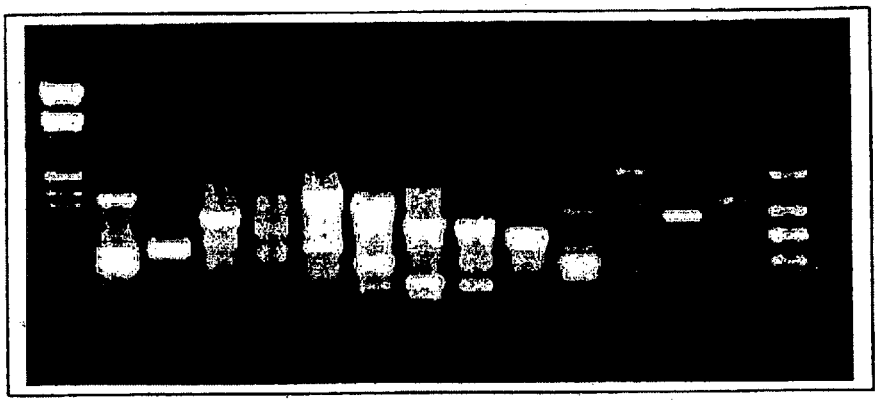

Figure 2 shows Unique RAPD profile of 'Nima'
Lane 1: l Hind III + EcoRI marker
Lane 2-15: Profiles with primers MAP 01, MAP 02, MAP 04, MAP 05, MAP 06, MAP 09, MAP 10, MAP 11, MAP 12, MAP 15, MAP 16, MAP 17, MAP 18, MAP 19.